US007199249B2

(12) United States Patent
Liu et al.

(10) Patent No.: US 7,199,249 B2
(45) Date of Patent: Apr. 3, 2007

(54) FREE RADICALLY POLYMERIZABLE COUPLING AGENTS

(75) Inventors: Puwei Liu, San Diego, CA (US); Stephen M. Dershem, San Diego, CA (US); Benjamin Neff, San Diego, CA (US); Maria Villegas, San Diego, CA (US)

(73) Assignee: Henkel Corporation, Rocky Hill, CT (US)

( * ) Notice: Subject to any disclaimer, the term of this patent is extended or adjusted under 35 U.S.C. 154(b) by 0 days.

(21) Appl. No.: 10/190,299

(22) Filed: Jul. 3, 2002

(65) Prior Publication Data

US 2004/0006166 A1 Jan. 8, 2004

(51) Int. Cl.
*C07F 7/10* (2006.01)
*C07F 7/18* (2006.01)
*C07D 207/24* (2006.01)

(52) U.S. Cl. ...................... 548/406; 556/407; 556/465; 428/355 R

(58) Field of Classification Search ................ 556/400, 556/407, 465; 525/331.9, 342; 548/406, 548/400; 428/355 R
See application file for complete search history.

(56) References Cited

U.S. PATENT DOCUMENTS

| | | | | |
|---|---|---|---|---|
| 3,755,354 | A * | 8/1973 | Holub et al. | 548/406 |
| 4,094,853 | A * | 6/1978 | Monte et al. | 523/202 |
| 4,271,074 | A | 6/1981 | Lohmann et al. | |
| 4,301,075 | A * | 11/1981 | Lohmann et al. | 548/548 |
| 4,565,873 | A | 1/1986 | Lohmann et al. | |
| 4,623,738 | A * | 11/1986 | Sugerman et al. | 556/17 |
| 5,240,992 | A * | 8/1993 | Yamaya | 524/806 |
| 5,447,988 | A | 9/1995 | Dershem et al. | 524/780 |
| 5,717,034 | A | 2/1998 | Dershem et al. | 525/276 |
| 5,789,757 | A | 8/1998 | Husson, Jr. et al. | 252/183.11 |
| 5,969,036 | A | 10/1999 | Dershem | 524/779 |
| 6,034,194 | A | 3/2000 | Dershem et al. | 526/262 |
| 6,034,195 | A | 3/2000 | Dershem et al. | 526/262 |
| 6,191,286 | B1 * | 2/2001 | Gunther et al. | 548/548 |
| 6,255,404 | B1 * | 7/2001 | Hogan et al. | 525/326.5 |
| 6,465,581 | B1 * | 10/2002 | Wideman et al. | 525/332.7 |

FOREIGN PATENT DOCUMENTS

| | | | |
|---|---|---|---|
| EP | 0 097 364 | A | 1/1984 |
| EP | 0 304 701 | A | 3/1989 |
| EP | 0 503 975 | A | 9/1992 |
| EP | 0 508 610 | A | 10/1992 |
| JP | 01 029385 | A | 1/1989 |
| JP | 05 088372 | A | 4/1993 |
| JP | 09 329893 | A | 12/1997 |
| JP | 11-322816 | A * | 11/1999 |
| JP | 11 322816 | A | 11/1999 |

OTHER PUBLICATIONS

Aldrich Chemical Catalog (1998-1999), pp. 35, 52, and 1052.*
Aldrich Catalogue (1998-1999) p. 1031.*
International Search Report for International Application No. PCT/US03/21425.

* cited by examiner

*Primary Examiner*—David W. Wu
*Assistant Examiner*—Rip A. Lee
(74) *Attorney, Agent, or Firm*—Steven C. Bauman

(57) ABSTRACT

In accordance with the present invention, there are provided novel coupling agents which are compatible with a wide variety of adhesive formulations and which provide substantial adhesion enhancement relative to base formulations to which they are added. Invention compounds comprise at least one free-radically polymerizable group (other than acrylate) and at least one reactive moiety which forms covalent bond(s) with substrates having free hydroxyl groups on the surface thereof. Thus, invention compounds are covalently linked to adhesive formulations upon free radical cure, while at the same time providing "residual" functionality which is capable of undergoing reaction with any substrate having reactive (e.g., hydroxyl) groups in the surface thereof.

13 Claims, 3 Drawing Sheets

FREE RADICALLY POLYMERIZABLE COUPLING AGENTS

FIELD OF THE INVENTION

The current invention relates to coupling agents (also called adhesion promoters) that contain at least one free-radically polymerizable functionality and at least one reactive functionality which promotes adhesion to substrates.

BACKGROUND OF THE INVENTION

Coupling agents have been employed in efforts to improve the performance of various adhesive and coating formulations. Such materials seek to improve the compatibility of adhesive formulations and the surfaces with which the adhesive is contacted.

Many different types of coupling agents have been employed in the past. Each provides potential benefits and potential limitations, depending on the particular formulations to which they are added and the substrate(s) to which adhesion is desired. Indeed, many of these coupling agents are based on epoxy or urethane resin systems. Therefore, in spite of the large number of coupling agents which already exist, there remains a need in the art for coupling agents which provide good compatibility with adhesive formulations such as free-radically curable systems, and which provide excellent adhesion enhancement to the base formulation to which it is added. The present invention addresses this and other needs as will become readily apparent upon review of the detailed description of the invention together with the figures and claims.

SUMMARY OF THE INVENTION

In accordance with the present invention, there are provided novel coupling agents which are compatible with a wide variety of adhesive and coating formulations and which provide substantial adhesion enhancement relative to base formulations to which they are added. In one aspect of the invention, invention compounds comprise at least one free-radically polymerizable group (other than acrylate) and at least one reactive moiety which forms hydrogen and/or covalent bond(s) with substrates having free hydroxyl groups on the surface thereof. In another aspect of the invention, invention compounds comprise at least one free-radically polymerizable group (other than acrylate) and at least one hydrolyzable moiety which forms hydrogen and/or covalent bond(s) with various substrates. Thus, invention compounds are covalently linked to adhesive formulations upon free radical cure, while at the same time providing "residual" functionality which is capable of undergoing reaction with any substrate having reactive (e.g., hydroxyl) groups in the surface thereof.

DETAILED DESCRIPTION OF THE INVENTION

Figure 1:
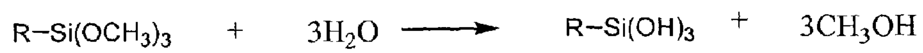
FIG. 1 illustrates the hydrolysis of an exemplary reactive moiety, Z, upon exposure to moisture.
Figure 2:
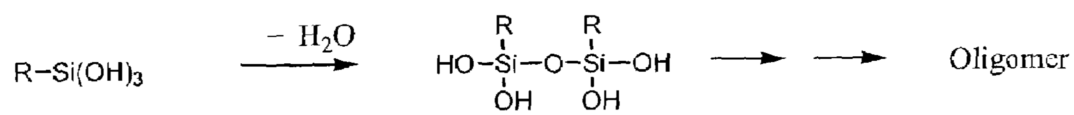
FIG. 2 illustrates the condensation of a plurality of hydrolysis products produced as illustrated in FIG. 1.

In accordance with the present invention, there are provided free-radically polymerizable compounds having the structure:

$$A_a\text{-}L\text{-}Z_b$$

wherein:

each A is independently a free-radically polymerizable group, provided however, that no A is acrylate, each L is independently a covalent bond or a polyvalent organic radical, each Z is independently a moiety reactive with hydroxyl groups (e.g., said moiety may form hydrogen and/or covalent bond(s) with substrates having free hydroxyl groups on the surface thereof), a is 1–200, and b is 1–200.

Free-radically polymerizable functionalities, A, contemplated for use in the practice of the present invention include optionally substituted maleimides, optionally substituted vinyl ethers, optionally substituted vinyl thioether, optionally substituted vinyl esters, optionally substituted fumarates, optionally substituted vinyl thioester, optionally substituted diallyl amides, optionally substituted styrene functional groups, optionally substituted polybutadienyl, and the like. These functional groups can co-cure by a free-radical mechanism with bismaleimide or acrylate resin systems when catalyzed by a small amount of free-radical inhibitor. Alternatively, such functional groups can also co-cure with bismaleimide or acrylate resin systems without using free radical initiator if the system is exposed to elevated cure temperatures, uv radiation, or the like.

As used herein, the term "optionally substituted maleimides" refers to compounds having the following structure:

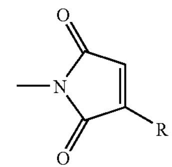

wherein R is independently selected from hydrogen or lower alkyl.

As used herein, the term "optionally substituted vinyl ethers" refers to compounds having the following structure:

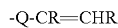

wherein each R is independently selected from hydrogen or lower alkyl, and Q is —O—.

As used herein, the term "optionally substituted vinyl thioether" refers to compounds of structure 1 wherein Q is —S—.

As used herein, the term "optionally substituted vinyl esters" refers to compounds of structure 1 wherein Q is —C(O)—O—.

As used herein, the term "optionally substituted fumarate" refers to compounds having the structure:

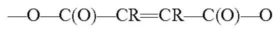

—O—C(O)—CR=CR—C(O)—O wherein each R is H, lower alkyl or substituted lower alkyl.

As used herein, the term "optionally substituted vinyl thioester" refers to compounds of structure 1 wherein Q is —O—C(S)— or —C(S)—O—.

As used herein, the term "optionally substituted diallyl amide" refers to compounds having the structure:

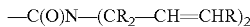

—C(O)N—($CR_2$—CH=CHR)$_2$ wherein each R is independently H, alkyl or substituted alkyl.

As used herein, the term "optionally substituted styrene functional groups" refers to compounds of the following structure:

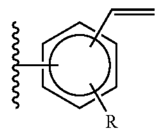

wherein R is as defined above.

As used herein, the term "optionally substituted polybutadienyl" refers to compounds of the following structure:

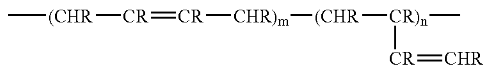

wherein R is as defined above, and m and n, taken together, are selected so as to provide a reactive moiety having a molecular weight in the range of about 200 up to about 10,000.

In accordance with the present invention, linker, L, can be a covalent bond, an organic radical having 1 up to 500 atoms in the backbone thereof, and the like.

Organic radicals contemplated for use in the practice of the present invention include straight or branched chain alkylene, alkylene oxide, alkylene amine, alkylene sulfide, alkylene ester, alkenylene, alkenylene oxide, alkenylene amine, alkenylene sulfide, alkenylene ester, arylene, arylene oxide, arylene amine, arylene sulfide, arylene ester, polysiloxane, and the like.

As used herein, the term "alkylene" refers to divalent straight, branched chain or cyclic hydrocarbyl radicals having 1 up to about 50 carbon atoms, preferably 2–20 carbon atoms; and "substituted alkylene" comprises alkylene groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As used herein, the term "alkylene oxide" refers to an alkylene moiety wherein one or more of the methylene units of the alkylene moiety has been replaced with an oxygen atom, and substituted alkylene oxide refers to alkylene oxide groups further bearing one or more substituents as set forth above.

As used herein, the term "alkylene amine" refers to an alkylene moiety wherein one or more of the methylene units of the alkylene moiety has been replaced with an amino group (—N—R), and substituted alkylene amine refers to alkylene amine groups further bearing one or more substituents as set forth above.

As used herein, the term "alkylene sulfide" refers to an alkylene moiety wherein one or more of the methylene units of the alkylene moiety has been replaced with a sulfur atom, and substituted alkylene sulfide refers to alkylene sulfide groups further bearing one or more substituents as set forth above.

As used herein, the term "alkylene ester" refers to an alkylene moiety wherein one or more of the methylene units of the alkylene moiety has been replaced with a carboxy moiety (—C(O)—O— or —O—C(O)—), and substituted alkylene ester refers to alkylene ester groups further bearing one or more substituents as set forth above.

As used herein, the term "alkenylene" refers to divalent, straight or branched chain hydrocarbyl groups having at least one carbon-carbon double bond, and having in the range of about 2 up to 12 carbon atoms, and "substituted alkenylene" refers to alkenylene groups further bearing one or more substituents as set forth above.

As used herein, the term "alkenylene oxide" refers to an alkenylene moiety wherein one or more of the methylene units of the alkenylene moiety has been replaced with an oxygen atom, and substituted alkenylene oxide refers to alkenylene oxide groups further bearing one or more substituents as set forth above.

As used herein, the term "alkenylene amine" refers to an alkenylene moiety wherein one or more of the methylene units of the alkenylene moiety has been replaced with an amino group, and substituted alkenylene amine refers to alkenylene amine groups further bearing one or more substituents as set forth above.

As used herein, the term "alkenylene sulfide" refers to an alkenylene moiety wherein one or more of the methylene units of the alkenylene moiety has been replaced with a sulfur atom, and substituted alkenylene sulfide refers to alkenylene sulfide groups further bearing one or more substituents as set forth above.

As used herein, the term "alkenylene ester" refers to an alkenylene moiety wherein one or more of the methylene units of the alkenylene moiety has been replaced with a carboxy moiety (—C(O)—O— or —O—C(O)—), and substituted alkenylene ester refers to alkenylene ester groups further bearing one or more substituents as set forth above.

As used herein, the term, "arylene" refers to divalent aromatic groups having in the range of 3 up to 14 carbon atoms (and optionally one or more heteroatoms such as N, S or O), and "substituted arylene" refers to arylene groups further bearing one or more substituents as set forth above.

As used herein, the term "arylene oxide" refers to an arylene moiety having at least one —O— substituent thereon, and substituted arylene oxide refers to arylene oxides further bearing one or more substituents as set forth above.

As used herein, the term "arylene amine" refers to an arylene moiety having at least one —NR— substituent thereon, and substituted arylene amine refers to arylene amines further bearing one or more substituents as set forth above.

As used herein, the term "arylene sulfide" refers to an arylene moiety having at least one —S— substituent thereon, and substituted arylene sulfide refers to arylene sulfides further bearing one or more substituents as set forth above.

As used herein, the term "arylene ester" refers to an arylene moiety having at least one carboxy moiety (—C(O)—O— or —O—C(O)—) thereon, and substituted arylene ester refers to arylene esters further bearing one or more substituents as set forth above.

As used herein, the term "polysiloxane" refers to compounds having the structure:

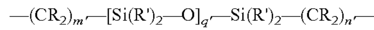

$—(CR_2)_{m'}—[Si(R')_2—O]_{q'}—Si(R')_2—(CR_2)_{n'}—$ or

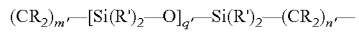

$(CR_2)_{m'}—[Si(R')_2—O]_{q'}—Si(R')_2—(CR_2)_{n'}—$ wherein each R is independently defined as above, and each R' is independently selected from hydrogen, lower alkyl or aryl, m' falls in the range of 1 up to 10, n' falls in the range of 1 up to 10, and q' falls in the range of 1 up to 50.

Figure 3:
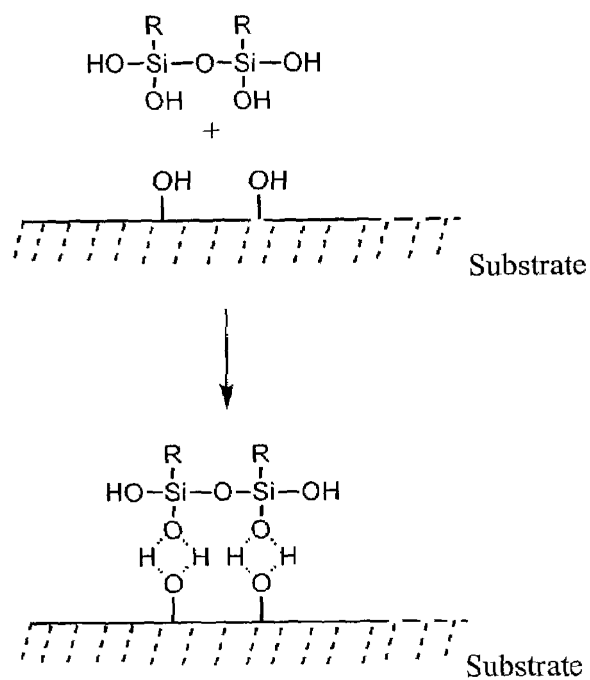
FIG. 3 illustrates the initial interaction of the condensation product produced as illustrated in FIG. 2 with free hydroxyl groups on the surface of a substrate.
Figure 4:
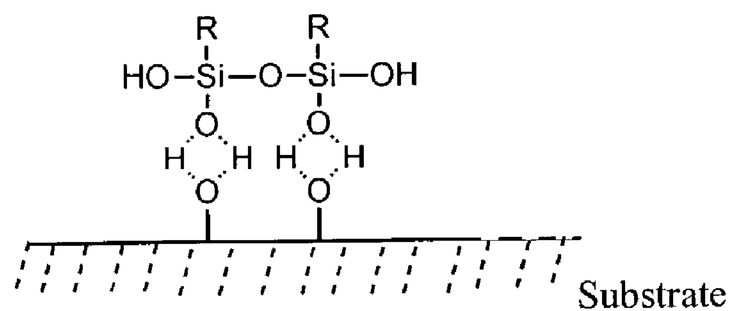
FIG. 4 illustrates the condensation of reactive moiety with substrate to produce a reactive moiety covalently bound to the surface of a substrate.
Figure 4:
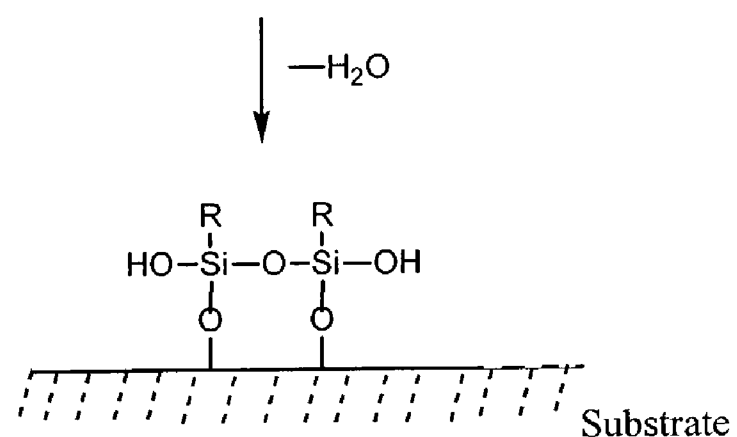
Figure 5:
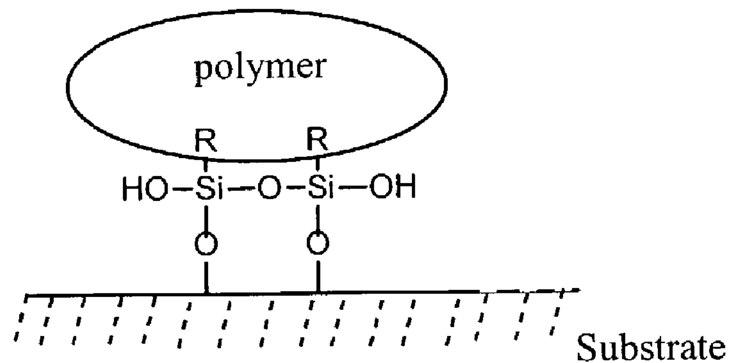
FIG. 5 illustrates a polymerized reactive moiety covalently bound to a substrate.

Reactive moieties, Z, contemplated for use in the practice of the present invention are groups which are capable of interacting, directly or indirectly, with hydroxyl groups, e.g., by formation of hydrogen bonds and/or covalent bonds (see FIGS. 3, 4 and 5). Such reactive moieties include hydrolyzable groups which are capable of interacting with the surface of substrate by way of hydrogen and/or covalent bonds. Exemplary reactive moieties include silanes, metal acrylate salts, titanates, aluminates, zirconates, tin oxides, nickel oxides, chelating groups, and the like.

Exemplary silanes contemplated for use in the practice of the present invention have the structure:

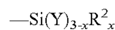

$—Si(Y)_{3-x}R^2_x$ wherein:

each Y is independently $OR^1$, $O—C(O)—R^1$, $NR_2$, or a halogen, each R is as defined above, each $R^1$ is independently an optionally substituted alkyl or aryl, each $R^2$ is independently an optionally substituted alkyl or aryl, halogen, and x=0, 1 or 2.

In one aspect of the invention, Y is $OR^1$ and x=0, so that Z is $—Si(OR^1)_3$, wherein $R^1$ is as defined above. In a presently preferred aspect of the invention each $R^1$ is independently lower alkyl.

In another aspect of the invention, Y is $OR^1$ and x=1, so that Z is $—Si(OR^1)_2R^2$, wherein $R^1$ and $R^2$ are as defined above. In a presently preferred aspect of the invention, each $R^1$ is independently lower alkyl and $R^2$ is halogen or lower alkyl.

In yet another aspect of the invention, Y is $OR^1$ and x=2, so that Z is $—Si(OR^1)R^2_2$, wherein $R^1$ and $R^2$ are as defined above. In a presently preferred aspect of the invention, $R^1$ is lower alkyl and each $R^2$ is independently halogen or lower alkyl.

Exemplary titanates contemplated for use in the practice of the present invention have the following structure:

$—Ti(OR^1)_{3-y}R^2_y$ wherein:

each $R^1$ is independently an optionally substituted alkyl or aryl, each $R^2$ is independently an optionally substituted alkyl or aryl, halogen, and y=0,1, or 2.

Exemplary aluminates contemplated for use in the practice of the present invention have the following structure:

$—Al(OR^1)_{2-x}R^2_x$ wherein:

each $R^1$ is independently an optionally substituted alkyl or aryl, each $R^2$ is independently an optionally substituted alkyl or aryl, halogen, and x is 0 or 1.

Exemplary zirconates contemplated for use in the practice of the present invention have the following structure:

$—Zr(OR^1)_{3-y}R^2_y$ wherein:

each $R^1$ is independently an optionally substituted alkyl or aryl, each $R^2$ is independently an optionally substituted alkyl or aryl, halogen, and y=0, 1, or 2.

Exemplary tin oxides contemplated for use in the practice of the present invention have the following structure:

$—Sn(OR^1)_{3-y}R^2_y$ wherein:

each $R^1$ is independently an optionally substituted alkyl or aryl, each $R^2$ is independently an optionally substituted alkyl or aryl, halogen, and y=0, 1, or 2.

Exemplary nickel oxides contemplated for use in the practice of the present invention have the following structure:

$—Ni(OR^1)$ wherein:

each $R^1$ is independently an optionally substituted alkyl or aryl.

Exemplary chelating groups include phosphines, mercaptans, acetoacetates, and the like.

In accordance with the present invention, a few up to a large number of free-radically polymerizable groups, A, can be present. Broadly, "a" can vary from 1 up to about 200, with in the range of 1–100 being preferred, and 1–20 being presently most preferred.

Similarly, in accordance with the present invention, a few up to a large number of reactive moieties, Z, can be present. Broadly, "b" can vary from 1 up to about 200, with in the range of 1–100 being preferred, and 1–20 being presently most preferred.

In accordance with another embodiment of the present invention, there are provided curable formulations comprising a free-radically polymerizable adhesive and an adhesion enhancing amount of an invention compound as described herein. As readily recognized by those of skill in the art, a wide variety of formulations can be enhanced by addition thereto of invention compounds, such as for example, die-attach adhesives, underfill, film adhesives, pressure sensitive adhesives, coating formulations, and the like.

Invention curable formulations optionally contain at least one free radical initiator, at least one filler, anti-oxidants, bleed control agents, inert (i.e., nonreactive) diluents, reactive diluents, toughening agents, coupling agents, adhesion promoters, flexibilizers, dyes, pigments, and the like.

As employed herein, the term "polymerization promoter" refers to curing agents, co-curing agents, catalysts, initiators or other additives designed to participate in or promote curing of the adhesive formulation. Such polymerization promoters include curing agents and catalysts such as, for example, free-radical curing agents (e.g., peroxides), hydrosilation agents, polythiols, and the like.

As readily recognized by those of skill in the art, the quantity of polymerization promoters employed in the practice of the present invention can vary widely, depending on a variety of factors, such as, for example, the base formulation, the presence of other reactive moieties, the rate of cure desired, and the like. Typically, the quantity of promoter employed will fall in the range of about 0.1 weight % up to about 10 weight % of the total composition, with in the range of about 0.1 weight % up to about 5 weight % of the total composition being presently preferred.

Fillers contemplated for optional use in the practice of the present invention may optionally be conductive (electrically and/or thermally). Electrically conductive fillers contemplated for use in the practice of the present invention include, for example, silver, nickel, gold, cobalt, copper, aluminum, graphite, silver-coated graphite, nickel-coated graphite, alloys of such metals, and the like, as well as mixtures thereof. Both powder and flake forms of filler may be used in the adhesive compositions of the present invention. Preferably, the flake has a thickness of less than about 2 microns, with planar dimensions of about 20 to about 25 microns. Flake employed herein preferably has a surface area of about 0.15 to 5.0 $m^2/g$ and a tap density of about 0.4 up to about 5.5 g/cc. It is presently preferred that powder employed in the practice of the invention has a diameter of about 0.5 to 15 microns. If present, the filler typically comprises in the range of about 30% up to about 90% by weight of the adhesive formulation.

Thermally conductive fillers contemplated for optional use in the practice of the present invention include, for example, aluminum nitride, boron nitride, silicon carbide, silicon nitride, diamond, graphite, beryllium oxide, magnesia, silica, alumina, and the like. Preferably, the particle size of these fillers will be about 20 microns. If aluminum nitride is used as a filler, it is preferred that it be passivated via an adherent, conformal coating (e.g., silica, or the like).

Electrically and/or thermally conductive fillers are optionally (and preferably) rendered substantially free of catalytically active metal ions by treatment with chelating agents, reducing agents, nonionic lubricating agents, or mixtures of such agents. Such treatment is described in U.S. Pat. No. 5,447,988, which is incorporated by reference herein in its entirety.

Optionally, a filler may be used that is neither an electrical nor thermal conductor. Such fillers may be desirable to impart some other property to the adhesive formulation such as, for example, reduced thermal expansion of the cured adhesive, reduced dielectric constant, improved toughness, increased hydrophobicity, and the like. Examples of such fillers include perfluorinated hydrocarbon polymers (i.e., TEFLON™), thermoplastic polymers, thermoplastic elastomers, mica, fused silica, glass powder, and the like.

Anti-oxidants contemplated for use in the practice of the present invention include hindered phenols (e.g., BHT (butylated hydroxytoluene), BHA (butylated hydroxyanisole), TBHQ (tertiary-butyl hydroquinone), 2,2'-methylenebis(6-tertiarybutyl-p-cresol), and the like), hindered amines (e.g., diphenylamine, N,N'-bis(1,4-dimethylpentyl-p-phenylene diamine, N-(4-anilinophenyl) methacrylamide, 4,4'-bis($\alpha,\alpha$-dimethylbenzyl) diphenylamine, and the like), phosphites, and the like. When used, the quantity of anti-oxidant typically falls in the range of about 100 up to 2000 ppm, relative to the weight of the base formulation.

Bleed control agents contemplated for use in the practice of the present invention include cationic surfactants, tertiary amines, tertiary phosphines, amphoteric surfactants, polyfunctional compounds, and the like, as well as mixtures of any two or more thereof. Those of skill in the art recognize that the quantity of bleed control agent employed in the practice of the present invention can vary widely, typically falling in the range of about 0.1 up to about 10 wt %, relative to the weight of the base formulation.

While the use of inert diluents is not excluded from the practice of the present invention, it is generally preferred that compositions according to the invention remain substantially free of solvent, so as to avoid the potentially detrimental effects thereof, e.g., creation of voids caused by solvent escape, the environmental impact of vaporized solvent, the redeposition of outgassed molecules in the surface of the article, and the like. When used, suitable inert diluents include dimethylformamide, dimethylacetamide, N-methylpyrrolidone, toluene, xylene, methylene chloride, tetrahydrofuran, glycol ethers, methyl ethyl ketone or monoalkyl or dialkyl ethers of ethylene glycol, polyethylene glycol, propylene glycol, polypropylene glycol, and the like. When used, inert diluents are typically present in the range of about 10 up to 40 wt %, relative to the weight of the base formulation.

Reactive diluents contemplated for use in the practice of the present invention include any reactive diluent which, in combination with the formulations described herein, forms a thermosetting resin composition. Such reactive diluents include acrylates and methacrylates of monofunctional and polyfunctional alcohols, ethylenically unsaturated compounds, styrenic monomers (i.e., ethers derived from the reaction of vinyl benzyl chlorides with mono-, di-, or trifunctional hydroxy compounds), and the like. When used, reactive diluents are typically present in the range of about 5 up to 15 wt %, relative to the weight of the base formulation.

Toughening agents contemplated for optional use in the practice of the present invention are reactive moieties modified to include an elastomeric component, thereby imparting resilience to the resulting formulation. Examples of such materials include epoxy-modified rubbers such as EPON resins, available from Resolution Performance Products (Houston, Tex.).

Flexibilizers (aka plasticizers) contemplated for optional use in the practice of the present invention include branched polyalkanes or polysiloxanes that lower the $T_g$ of the formulation. Such flexibilizers include, for example, polyethers, polyesters, polythiols, polysulfides, polybutadienes, and the like. If present in the adhesive formulation, flexibilizers typically comprise in the range of about 0% up to about 30% by weight of the formulation.

Dyes contemplated for use in the practice of the present invention include nigrosine, Orasol blue GN, phthalocyanines, and the like. When used, organic dyes in relatively low amounts (i.e., amounts less than about 0.2 wt %) provide contrast.

Pigments contemplated for use in the practice of the present invention include any particulate material added solely for the purpose of imparting color to the formulation, e.g., carbon black, metal oxides (e.g., $Fe_2O_3$, titanium oxide), and the like. When present, pigments are typically present in the range of about 0.5 up to about 5 wt %, relative to the weight of the base formulation.

In accordance with yet another embodiment of the present invention, there are provided methods for improving the adhesion of a free-radically polymerizable adhesive to a substrate. Invention methods comprise adding to said adhesive an adhesion-enhancing amount of an invention compound as described herein. As employed herein, the term "adhesion enhancing amount" refers to that amount of invention compound which provides a significant improvement in the adhesion of a formulation to which the compound is added. Typically, in the range of about 0.1–10 wt % of invention compound is added to an adhesive formulation; with in the range of about 0.5–5 wt % presently preferred; with in the range of about 1–2.5 presently most preferred.

In accordance with a further embodiment of the present invention, there are provided methods for improving the affinity of fillers for the resin system into which the filler is incorporated, said method comprising pre-treating filler with an invention coupling agent prior to incorporation thereof into the resin system. Pre-treatment can readily be carried out by contacting filler with coupling agent in suitable media (e.g., a solvent for the coupling agent) under fairly mild conditions (e.g., 0 up to about 100° C.), then drying the treated filler before incorporation into resin formulation.

In accordance with still another embodiment of the present invention, there are provided methods for adhesively attaching a first article to a second article. Invention methods comprise:

(a) applying an invention formulation as described herein to said first article, (b) bringing together said first article and said second article (i.e., bringing said first article and said second article into intimate contact with one another) to form an assembly wherein said first article and said second article are separated by the formulation applied in step (a) (preferably the formulation is the only thing that separates the two articles), and thereafter, (c) subjecting said assembly to conditions suitable to polymerize said formulation.

Those of skill in the art readily recognize conditions which are "suitable to polymerize" invention formulations. Such conditions typically comprise temperatures in the range of about 70 up to about 200° C. for 0.01 minutes up to several hours. Temperatures in the range of about 80 up to about 150° C. for 0.01 minutes up to about 30 minutes are presently preferred.

In accordance with yet another embodiment of the present invention, there are provided articles produced by the above-described method.

In accordance with a further embodiment of the present invention, there are provided methods for adhesively attaching a microelectronic device to a substrate. Invention methods comprise:

(a) applying an invention formulation as described herein to said substrate and/or said microelectronic device, (b) bringing together said substrate and said device (i.e., bringing said substrate and said device into intimate contact with one another) to form an assembly wherein said substrate and said device are separated by the formulation applied in step (a) (preferably the formulation is the only thing that separates the two components), and thereafter, (c) subjecting said assembly to conditions suitable to polymerize said formulation.

In accordance with still another embodiment of the present invention, there are provided articles produced by the above-described method.

In accordance with yet another embodiment of the present invention, there are provided assemblies comprising a first article permanently adhered to a second article by a cured aliquot of invention formulation as described herein.

In accordance with still another embodiment of the present invention, there are provided assemblies comprising a microelectronic device permanently adhered to a substrate by a cured aliquot of an invention formulation as described herein.

The invention will now be described in greater detail with reference to the following non-limiting examples.

EXAMPLE 1

Synthesis of maleimidopropyl trimethoxysilane

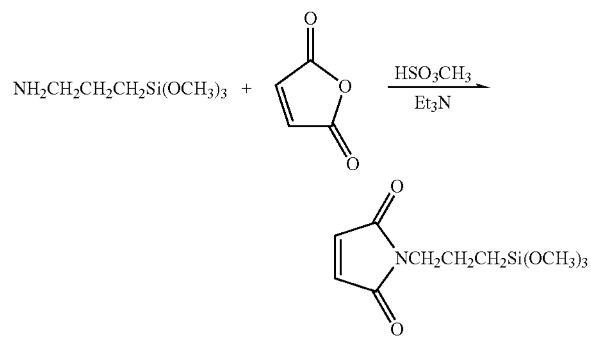

Triethylamine (24.6 g, 0.2 mol) and methanesulfonic acid (26.0 g, 0.26 mol) were placed into a three-neck round-bottom flask and dissolved in 200 ml of toluene. This mixture was stirred at room temperature for 30 minutes. Maleic anhydride (20.5 g, 0.21 mol) was then added to this mixture. After the maleic anhydride had dissolved, aminopropyl trimethoxysiloxane (35.8 g, 0.2 mol) was introduced. This mixture was heated to reflux while stirring for 24 hours and the water generated from this reaction was collected by a Dean-Stark trap.

The reaction mixture was then allowed to cool to room temperature, then the upper clear layer of this mixture was separated by a separation funnel. It was then passed through a filtration funnel with a thin layer of silica gel. The toluene was removed by vacuum to give a clear liquid. Yield: 36%.

EXAMPLE 2

Synthesis of maleimidopropyl triethoxysilane

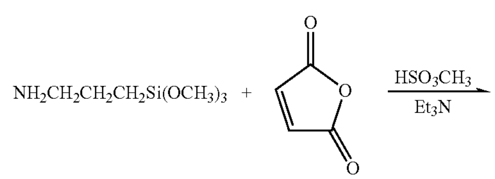

-continued

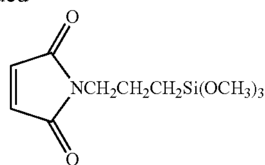

The experimental procedure described in Example 1 was repeated employing triethylamine (24.6 g, 0.2 mol), methanesulfonic acid (26.0 g, 0.26 mol), maleic anhydride (20.5 g, 0.21 mol), aminopropyl triethoxysiloxane (44.0 g, 0.2 mol), and 250 ml toluene. Yield: 38%.

EXAMPLE 3

Triethoxysilane Derivative of ethylene glycol divinyl ether

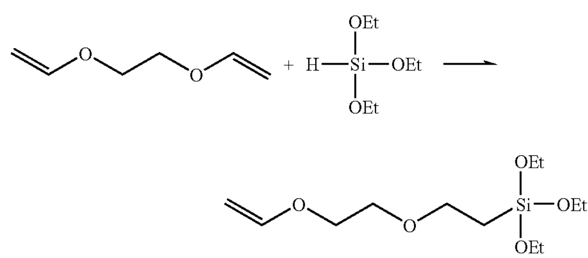

Ethylene glycol divinyl ether (22.0 g, 0.1 mol) and triethoxy silane (16.4 g, 0.1 mol) were placed into a 250 ml round-bottom flask containing 100 ml of toluene and a magnetic stirrer. Platinum-divinyl tetramethyldisiloxane (0.05 g) catalyst was added to this mixture, which was then stirred at room temperature for 30 minutes. The temperature of the reaction mixture was then raised to around 50° C. for 24 hours. FTIR spectrum of a sample from this mixture showed no absorption around 2200 $cm^{-1}$.

The reaction mixture was then passed through a filtration funnel with a thin layer of silica gel. The toluene was removed by vacuum to give a clear liquid. Yield: 92%.

EXAMPLE 4

Triethoxysilane Derivative of 5-vinyl-2-norbornene

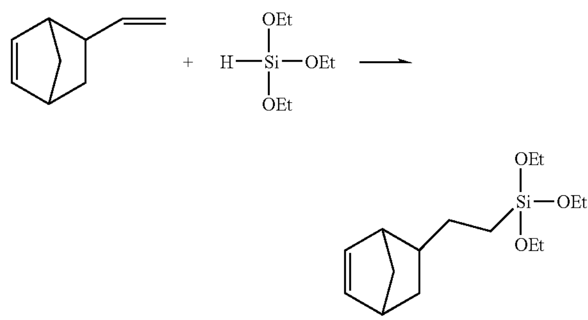

The experimental procedure described in Example 3 was repeated employing 5-vinyl-2-norbornene (60.0 g, 0.5 mol), triethoxysilane (32.0 g, 0.2 mol), platinum-divinyl tetramethyldisiloxane (0.1 g), and 200 ml of toluene. The final product is a slightly yellow liquid. Yield: 90%.

EXAMPLE 5

Synthesis of 3-methylmaleimidopropyl trimethoxysilane

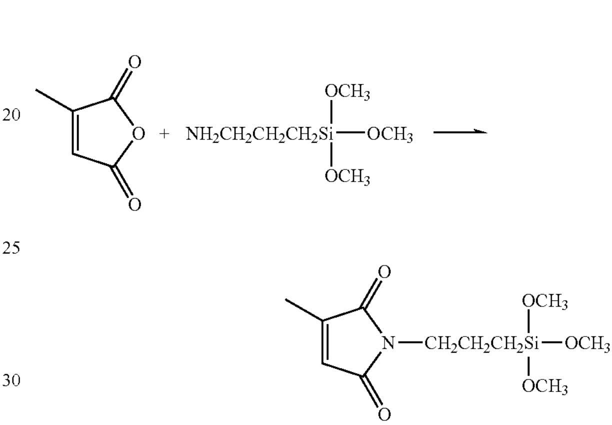

The experimental procedure described in Example 1 was repeated employing citraconic anhydride (25.0 g, 0.22 mol), aminopropyl trimethoxysilane (36.0 g, 0.20 mol), triethylamine (26.0 g, 0.24 mol), methanesulfonic acid (26.0 g, 0.26 mol), and 200 ml of toluene. The product was a yellow viscous liquid. Yield: 35%.

EXAMPLE 6

Synthesis of Polysilyl Compound X

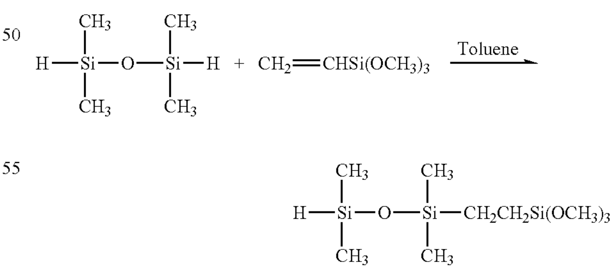

The experimental procedure described in Example 3 was repeated employing 1,1,3,3-tetramethyl disiloxane (5.93 g, 0.044 mol), vinyltrimethoxysilane (13.1 g, 0.088 mol), divinyl tetramethyldisiloxane (0.05 g), and 100 ml of toluene. The product was a clear liquid. Yield: 100%.

EXAMPLE 7

Silylated Polybutadiene

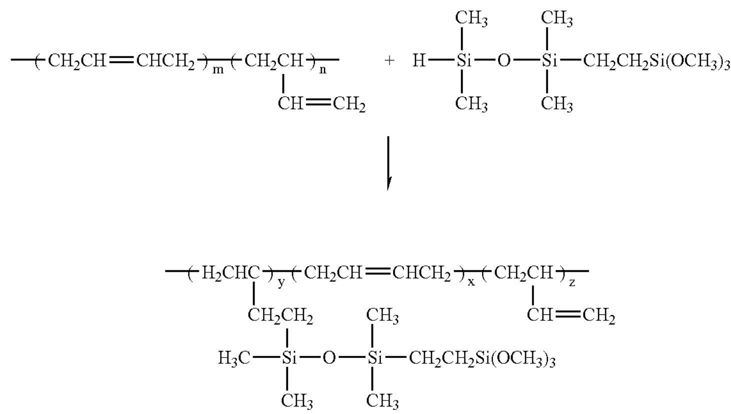

The experimental procedure described in Example 3 was repeated employing polybutadiene (of ~3000 molecular weight, with a 1,4/1,2 (i.e., m/n) ratio of about 4:1; 5.4 g), polysilyl compound X, prepared as described in Example 6 (14.1 g, 0.05 mol), divinyl tetramethyldisiloxane (0.05 g), and 100 ml of toluene. The product was a clear liquid. Yield: 96%.

EXAMPLE 8

Synthesis of Vinyl 11-undecenyl ether, XI

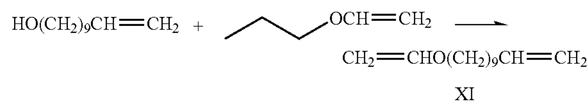

11-Undecenyl alcohol (90.0 g, 0.53 mol), vinyl propyl ether (500 g, 5.8 mol) and phenanthroline complex of Pd(II) acetate catalyst (0.2 g) were placed into a 2 L round bottom flask. This flask was placed on a rotary evaporator and was heated to 50° C. in a water bath for 48 hours while rotating. Then the vinyl ether was carefully removed under low vacuum and the residue was sparged with $N_2$ for 30 minutes. Another 500 g of fresh vinyl propyl ether, together with 100 mg catalyst, was added and this mixture was allowed to rotate in the 50° C. water bath for another 20 hours. Then vinyl ether was again carefully removed, and the residue sparged with $N_2$ for 30 minutes. Another 500 g of vinyl propyl ether and 100 mg of catalyst were added and the process repeated one more time for 20 hours. FTIR spectrum of the residue was completely flat at 3300 cm.

After removal of the vinyl propyl ether solvent by rotary evaporation, the red residue was dissolved in 200 ml of octane and passed through a thin layer of silica gel. The octane was removed by rotary evaporation to give a slightly yellow liquid. Yield: 90%.

EXAMPLE 9

Triethylsilyl Derivative of Compound XI

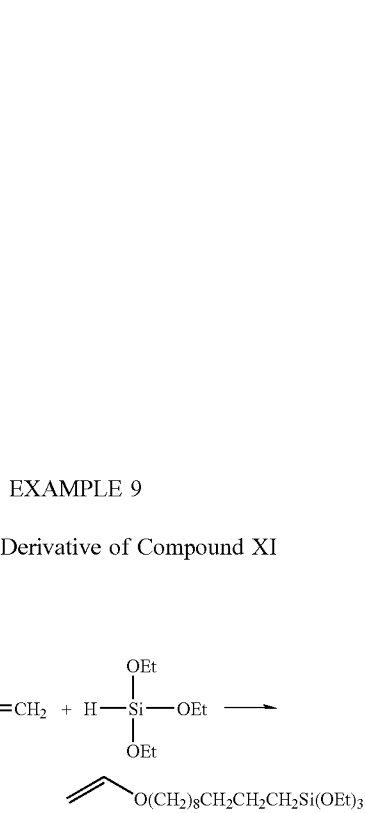

The experimental procedure described in Example 3 was repeated employing Compound XI, prepared as described in Example 8 (30.0 g, 0.15 mol), triethoxysilane (18.0 g, 0.15 mol), platinum-divinyl tetramethyldisiloxane (0.1 g), and 200 ml of toluene. The final product is a slightly yellow liquid. Yield: 83%.

EXAMPLE 10

Trimethylsilyl Derivative of Compound XI

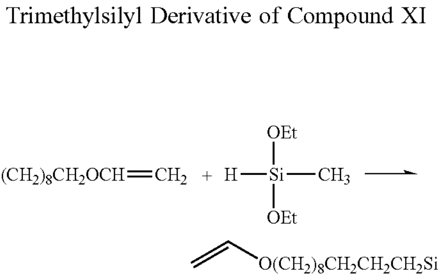

The experimental procedure described in Example 3 was repeated employing Compound XI, prepared as described in Example 8 (20.0 g, 0.1 mol), trimethoxysilane (12.2 g, 0.1 mol), platinum-divinyl tetramethyldisiloxane (0.1 g), and 200 ml of toluene. The final product is a slightly yellow liquid. Yield: 87%.

EXAMPLE 11

Di(11-undecenyl) fumarate, XII

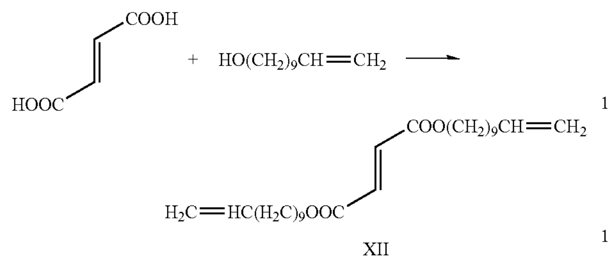

The experimental procedure described in Example 1 was repeated employing fumaric acid (26.0 g, 0.21 mol), methanesulfonic acid (3.0 g), 11-undecylenyl alcohol (68.0 g, 0.42 mol) g, and 250 ml of toluene. The product is a viscous liquid. Yield: 86%.

EXAMPLE 12

Di(11-trimethoxysilylundecenyl) fumarate

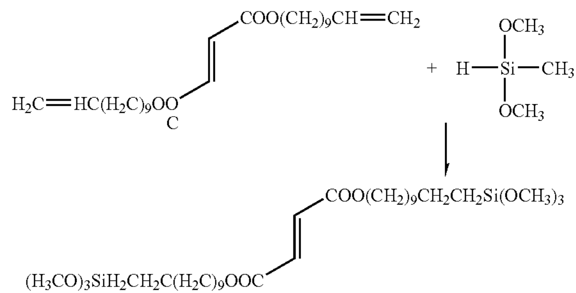

The experimental procedure described in Example 3 was repeated employing Compound XII, prepared as described in Example 11 (20.0 g, 0.1 mol), trimethoxysilane (12.2 g, 0.1 mol), platinum-divinyl tetramethyldisiloxane (0.1 g), and 200 ml of toluene. The final product is a slightly yellow liquid. Yield: 87%.

EXAMPLE 13

Di(11-triethoxysilylundecenyl) fumarate

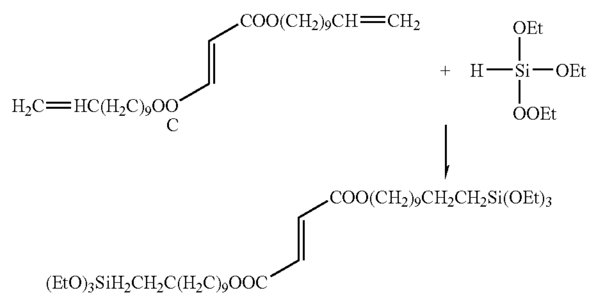

The experimental procedure described in Example 3 was repeated employing Compound XII, prepared as described in Example 11 (8.4 g, 20 mmol), triethoxysilane (4.64 g, 40 mmol), platinum-divinyl tetramethyldisiloxane (0.1 g), and 100 ml of toluene. The final product is a slightly yellow liquid. Yield: 70%.

EXAMPLE 14

Adhesion Test

Adhesion was evaluated using a tensile test method. The control formulation was a bismaleimide-based formulation, and test formulation was the same bismaleimide-based formulation, further containing 2–2.25 wt % of invention coupling agent. Aluminum studs (with a head diameter of 280 mils) were attached to clean copper slugs (1000×400×150 mils) using each of the test formulations as well as a control. Ten of these test assemblies were constructed for each formulation tested. The adhesive-test assemblies were processed by heating them in an air-circulating oven set at 200° C. for thirty minutes. The parts were allowed to cool to room temperature and the adhesive strength was determined using a tensile tester. The adhesion test results (pounds force) were converted to pounds per square inch based on the contact area of the aluminum stud. All values shown in Table 1 are averages for the ten test adhesive-test assemblies that were prepared for each formulation. Test results were normalized based on control adhesion determined each day to correct for day-to-day variations in the cure conditions.

The percent adhesion enhancement for each of the coupling agents additives was determined according to the equation:

$$\%\ \text{Enhancement}=[(\text{test mixture adhesion}\div\text{control adhesion})-\text{control adhesion}]\times 100$$

TABLE 1

| Coupling Agents | % Coupling Agent Added to Mixture | Adhesion (PSI) | Control Adhesion (PSI) | Adhesion Enhancement (%) |
|---|---|---|---|---|
| Example 4 | 2 | 50.8 | 27.8 | 83 |
| Example 2 | 2 | 34.5 | 18.1 | 90.6 |
| Example 12 | 2.5 | 42.2 | 18.1 | 133 |
| Example 10 | 2 | 54.1 | 28 | 93.2 |

As can be readily seen by inspection of the data in Table 1, all coupling agents tested gave a dramatic increase in adhesion to substrate.

EXAMPLE 15

Thermogravimetric Analysis (TGA)

Figure 6:
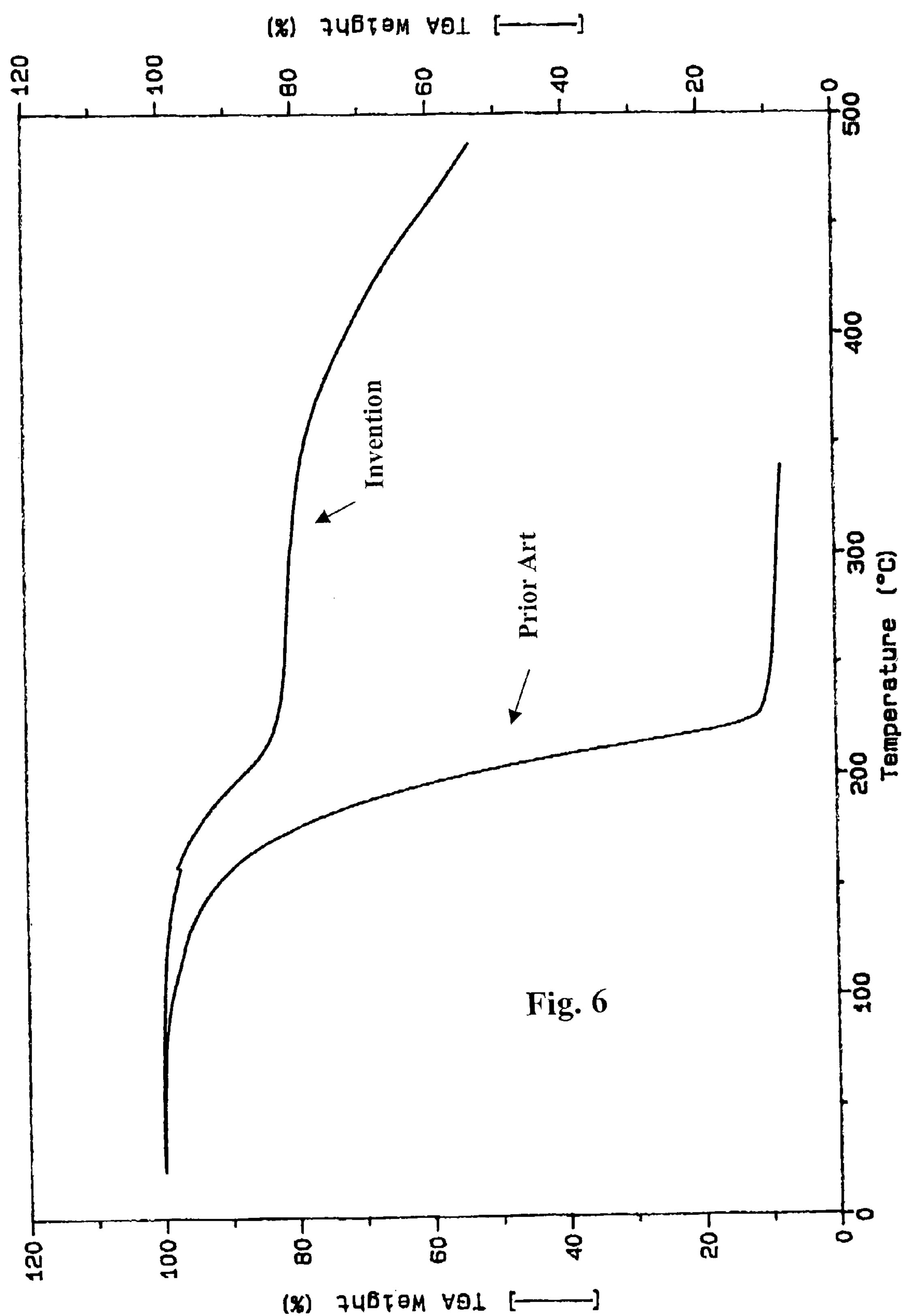
FIG. 6 presents the results of thermogravimetric analysis of an invention coupling agent (see Example 1) and a commercially available coupling agent (3-glycidoxypropyltrimethoxysilane).

The coupling agent prepared as described in Example 1, and a prior art coupling agent (3-glycidoxypropyltrimethoxysilane), were subjected to thermogravimetric analysis to determine the stability of these materials as the temperature thereof is increased. As can be seen upon inspection of FIG. 6, invention coupling agent is substantially less prone to weight loss than is the prior art coupling agent as the temperature thereof is elevated.

While the invention has been described in detail with reference to certain preferred embodiments thereof, it will be understood that modifications and variations are within the spirit and scope of that which is described and claimed.

What is claimed is:

1. A free-radically polymerizable compound having the structure:

$A_a$-L-$Z_b$ wherein:

each A is independently a free-radically polymerizable group selected from the group consisting of an optionally substituted maleimide, an optionally substituted vinyl ether, an optionally substituted vinyl thioether, an optionally substituted vinyl ester, an optionally substituted fumarate, an optionally substituted vinyl thioester, an optionally substituted diallylamide, an optionally substituted styrenyl, and a norbornyl, and at least one A is alkyl substituted maleimide, each L is independently a covalent bond or a polyvalent organic radical, each Z is a chelating group and is independently a moiety reactive with hydroxyl groups, and at least one Z is a silicate ester, a is 1–200, and b is 1–200, wherein said compound, when added to a free-radically polymerizable adhesive in an adhesion enhancing amount, enhances the adhesion of said adhesive to a substrate by at least 83%.

2. A compound according to claim 1 wherein said silicate ester has the structure:

—$Si(OR^1)_{3-x} R^2_x$ wherein:

each $R^1$ is independently an optionally substituted alkyl or aryl, each $R^2$ is independently an optionally substituted alkyl or aryl, halogen, and x=0, 1 or 2.

3. A compound according to claim 1, wherein L is a covalent bond.

4. A compound according to claim 1, wherein L is an organic radical having up to 500 atoms in the backbone thereof.

5. A compound according to claim 4 wherein L is an organic radical selected from the group consisting of a straight or branched chain alkylene, alkylene oxide, alkylene amine, alkylene sulfide, alkylene ester, alkenylene, alkenylene oxide, alkenylene amine, alkenylene sulfide, alkenylene ester, arylene, arylene oxide, arylene amine, arylene sulfide, arylene ester, and polysiloxane.

6. A compound according to claim 1, wherein Z is —$Si(OR^1)_3$, and wherein each $R^1$ is independently lower alkyl.

7. A compound according to claim 1, wherein Z is —$Si(OR^1)_2R^2$, wherein each $R^1$ is independently lower alkyl, and wherein $R^2$ is halogen or lower alkyl.

8. A compound according to claim 1, wherein Z is —$Si(OR^1)R^2_2$, wherein $R^1$ is lower alkyl, and wherein each $R^2$ is independently halogen or lower alkyl.

9. A compound according to claim 1, wherein a is 1–100.

10. A compound according to claim 9, wherein a is 1–20.

11. A compound according to claim 1, wherein b is 1–100.

12. A compound according to claim 11, wherein b is 1–20.

13. A free-radically polymerizable compound in a curable composition having the structure:

$A_a$-L-$Z_b$ wherein:

each A is independently a free-radically polymerizable group selected from the group consisting of an optionally substituted maleimide, an optionally substituted vinyl ether, an optionally substituted vinyl thioether, an optionally substituted vinyl ester, an optionally substituted fumarate, an optionally substituted vinyl thioester, an optionally substituted diallylamide, an optionally substituted styrenyl, and a norbornyl, each L is independently a covalent bond or a polyvalent organic radical, each Z is independently a chelating group moiety reactive with hydroxyl groups selected from the group consisting of a phosphine, a mercaptan and an acetoacetate, a is 1–200, and b is 1–200.

* * * * *